US00PP31425P2

(12) United States Plant Patent
Clark

(10) Patent No.: US PP31,425 P2
(45) Date of Patent: Jan. 28, 2020

(54) COLEUS PLANT NAMED 'UF15-97-9'

(50) Latin Name: *Plectranthus scutellarioides*
Varietal Denomination: UF15-97-9

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/350,114

(22) Filed: Sep. 26, 2018

(51) Int. Cl.
*A01H 6/50* (2018.01)
*A01H 6/00* (2018.01)
*A01H 5/00* (2018.01)

(52) U.S. Cl.
USPC ..... Plt./469

(58) Field of Classification Search
USPC ..... Plt./469
CPC ..... A01H 5/00; A01H 6/00; A01H 6/50
See application file for complete search history.

(56) References Cited

U.S. PATENT DOCUMENTS

PP28,566 P2 10/2017 Clark

OTHER PUBLICATIONS

U.S. Appl. No. 15/732,774, filed Dec. 27, 2017, Clark.
U.S. Appl. No. 15/732,779, filed Dec. 27, 2017, Clark.
U.S. Appl. No. 15/732,777, filed Dec. 27, 2017, Clark.
U.S. Appl. No. 15/732,776, filed Dec. 27, 2017, Clark.
U.S. Appl. No. 05/732,775, filed Dec. 27, 2017, Clark.
U.S. Appl. No. 15/732,778, filed Dec. 27, 2017, Clark.
U.S. Appl. No. 16/350,116, filed Sep. 26, 2018, Clark.
U.S. Appl. No. 16/350,113, filed Sep. 26, 2018, Clark.
Variety specific information as indicated in transmittal letter Information Disclosure Statement for U.S. Appl. No. 16/350,114, filed Mar. 26, 2019.
U.S. Appl. No. 15/732,775, filed Dec. 27, 2017, Clark.

*Primary Examiner* — Keith O. Robinson
(74) *Attorney, Agent, or Firm* — Dentons US LLP

(57) ABSTRACT

'UF15-97-9' is a new coleus plant with novel characteristics that include excellent heat tolerance, uniform crimson leaves that are uniquely lance-shaped, and a vigorous and compact upright growth habit with excellent lateral branching. 'UF15-97-9' also exhibits superior foliage color stability when grown in all conditions, including both sun and shade conditions, and exhibits long-season performance until late fall.

3 Drawing Sheets

Latin name of the genus and species of the plant claimed: *Plectranthus scutellarioides.*

Cultivar denomination: 'UF15-97-9'.

BACKGROUND OF THE INVENTION

The invention relates to a new and distinct cultivar of coleus plant that has been designated 'UF15-97-9'. This cultivar originated from an open pollination between the female coleus plant 'UF14-81-13' (unpatented) and an unknown male coleus plant. This open pollination was conducted in Gainesville, Fla. from May through November of 2014. Asexual propagation of 'UF15-97-9' first occurred in Gainesville, Fla. in May of 2015 using meristem tip cuttings. That and all subsequent asexual propagations of 'UF15-97-9' have remained true-to-type and retained the distinctive features of this novel cultivar.

SUMMARY OF THE INVENTION

The following are the most outstanding and distinguishing characteristics of 'UF15-97-9' when grown in Gainesville, Fla. under typical horticultural practices. 'UF15-97-9' exhibits excellent heat tolerance and uniform crimson leaves that are uniquely lance-shaped. 'UF15-97-9' also exhibits a vigorous and compact upright growth habit and excellent lateral branching, and thus provides ample vegetative propagules for producers when utilized as a stock plant. Also, 'UF15-97-9' exhibits superior foliage color stability when grown in all conditions, including both sun and shade conditions, and in landscape trials that were performed in Gainesville, Fla. 'UF15-97-9' exhibited long-season performance until late fall. Further, 'UF15-97-9' can easily grow over two feet tall and three feet wide when grown as a landscape fixture and still maintain similar size in both sun and shade.

'UF15-97-9' can be distinguished from its female parent, 'UF14-81-13', at least based upon leaf coloration and plant growth habit. 'UF15-97-9' exhibits leaves that are uniformly deep crimson with older and shaded foliage exhibiting occasional chartreuse flecking; whereas, 'UF14-81-13' exhibits leaves that are predominantly dark maroon with lime green margins. 'UF15-97-9' has a well-branched mounded habit and grows wider than it is tall; whereas, 'UF14-81-13' exhibits a more vigorous habit and grows taller than it is wide.

The coleus cultivar 'UF16-14-3' (unpatented, commercial trade name 'Cherry Brandy™'), also exhibits young and mature foliage that is similar in shape and color to that of 'UF15-97-9'. However, the leaves of 'UF16-14-3' are wider than those of 'UF15-97-9'; and the lobed leaf margins of 'UF16-14-3' are more rounded than those of 'UF15-97-9'.

Further, the leaves of 'UF16-14-3' do not exhibit the occasional chartreuse flecking along their tips that is characteristic of 'UF15-97-9'.

BRIEF DESCRIPTION OF THE DRAWINGS

This new coleus plant is illustrated by the accompanying photographs, which show the plant's form and foliage. The colors shown are as true as can be reasonably obtained by conventional photographic procedures. The photographs in FIGS. 2 and 3 are of plants that were grown from unrooted cuttings in a poly-covered plastic greenhouse in Gainesville, Fla. for 11 weeks from November, 2017 through February, 2018.

DETAILED BOTANICAL DESCRIPTION

Figure 1:
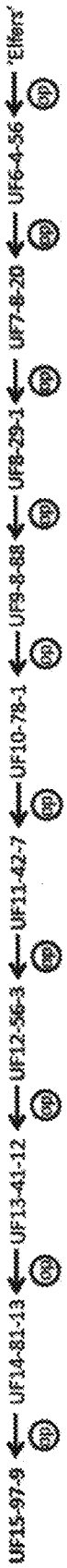
FIG. 1—Shows the pedigree of 'UF15-97-9'.
Figure 2:
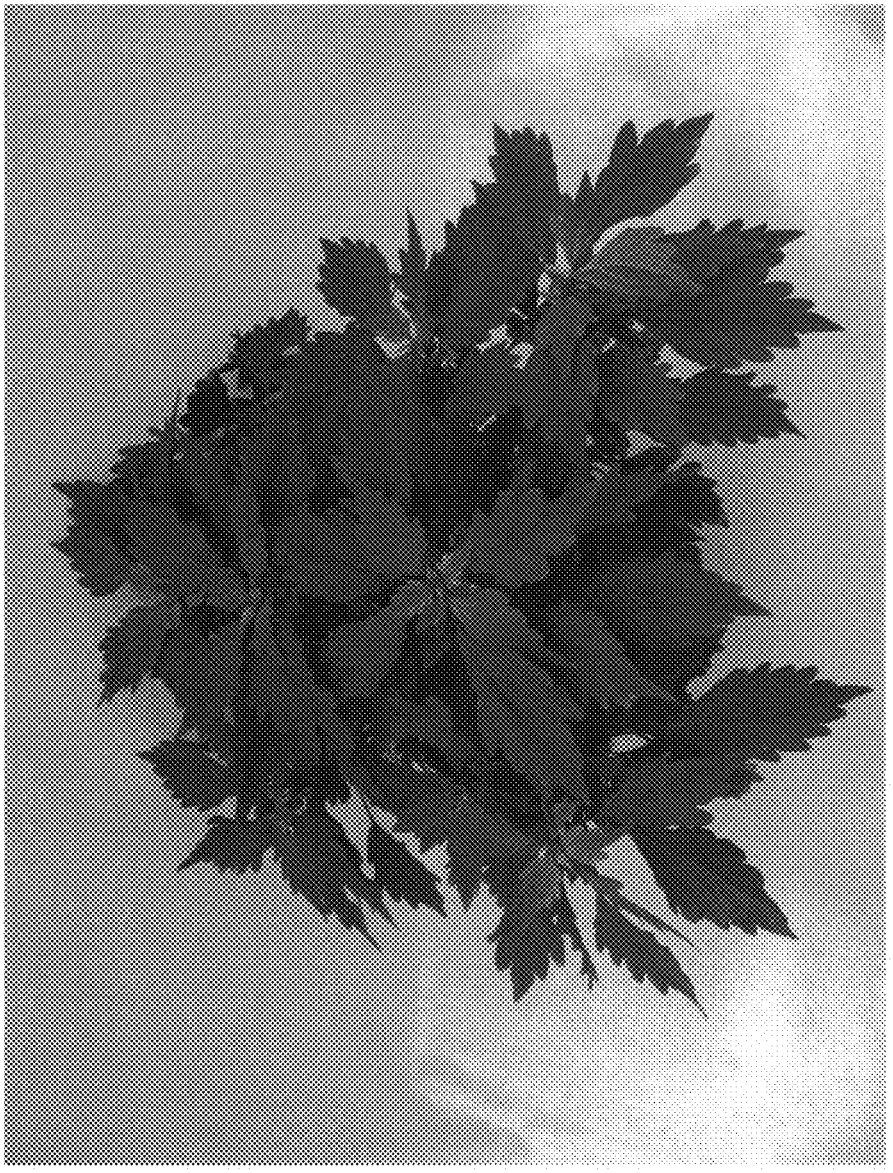
FIG. 2—Shows the growth habit, form, and foliage of 'UF15-97-9'.
Figure 3:
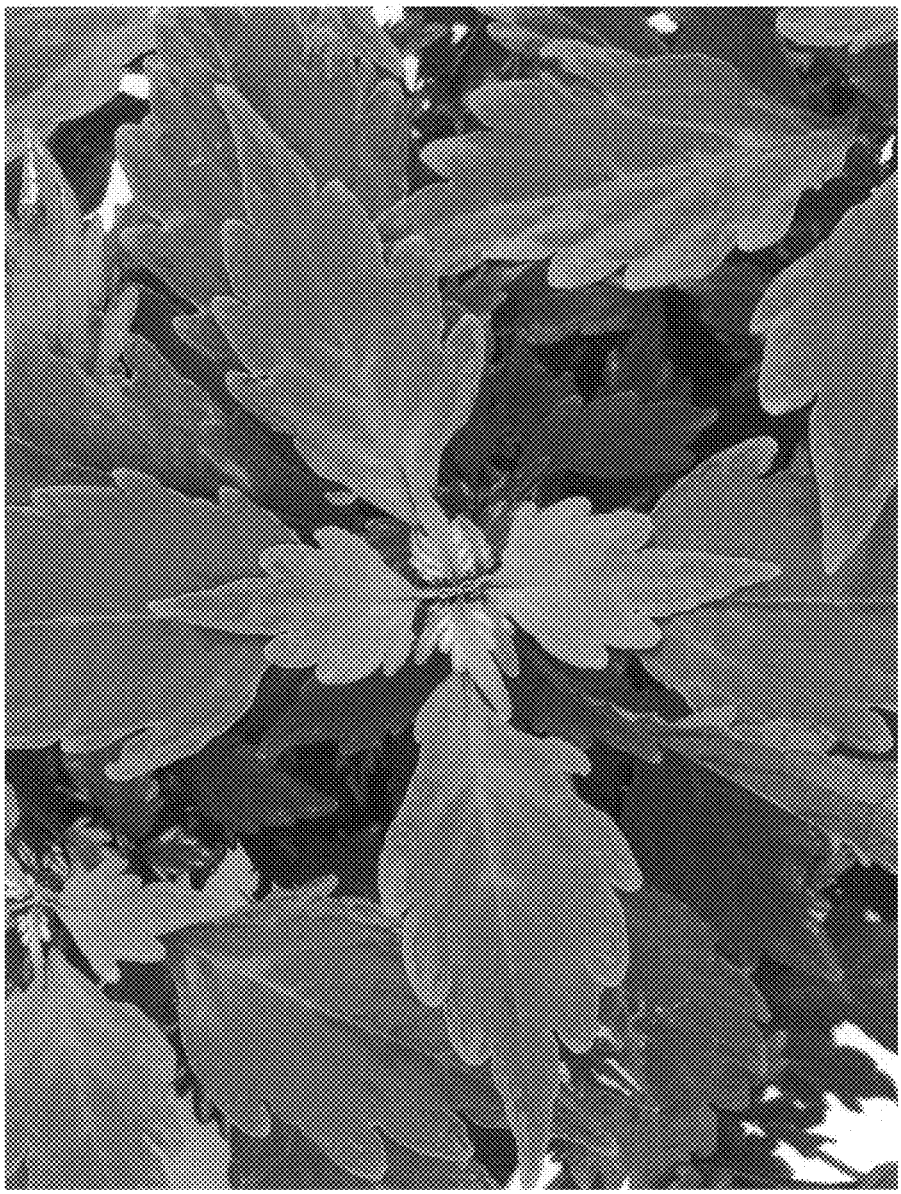
FIG. 3—Shows a close-up of the foliage of 'UF15-97-9'.

The following detailed description sets forth the distinctive characteristics of 'UF15-97-9'.The detailed description was obtained using 10-week-old plants grown from unrooted cuttings during November, 2017 through February, 2018 in a poly-covered plastic greenhouse in Gainesville, Fla. The plants were propagated in mist for 10 days after cuttings were stuck, and then they were grown in 1-gallon pots for approximately 9 weeks. Color references are to The RHS Colour Chart of The Royal Horticultural Society of London (RHS), 2007 5th Edition.

Classification:

*Family.*—Lamiaceae.

*Botanical.*—*Plectranthus scutellarioides.*

*Common name.*—Coleus.

*Cultivar name.*—'UF15-97-9'.

Plant description:

*Form.*—Spreading.

*Habit.*—Upright.

*Height* (*from top of soil*).—25-30 cm.

*Width* (*horizontal plant diameter*).—55-65 cm.

Propagation:

*Type cuttings.*—Vegetative meristems having at least 1 node.

*Time to initiate roots.*—3-4 days.

*Time to produce a rooted cutting.*—7-10 days.

*Root habit.*—Fibrous.

*Root description.*—Callus forms in 2-3 days; the roots initiate in 3-4 days; and roots become highly branched in 7-10 days.

Branches:

*Quantity per plant.*—7.

*Branch color.*—Greyish red, RHS N186C.

*Texture.*—Smooth.

*Pubescence.*—Not present.

*Stem description.*—Square-shaped and 0.5 cm diameter at the soil line.

*Branch diameter.*—0.4-0.5 cm at the base of a 23 cm long branch.

*Branch length.*—20-25 cm.

*Internode length.*—3-4 cm.

*Anthocyanin.*—Greyish red, RHS N186C.

Leaves:

*Quantity of leaves per branch.*—20-22. Arrangement: Opposite.

*Fragrance.*—Not fragrant.

*Shape.*—Ovate.

*Length.*—10-12 cm.

*Width.*—5-6 cm.

*Apex.*—Broadly acute.

*Base.*—Attenuate and oblique.

*Margin.*—Lobed.

*Leaf texture* (*both surfaces*).—Smooth.

*Pubescence color* (*both surfaces*).—Not present.

*Venation color.*—Upper surface: Greyish purple, RHS N187B. Lower surface: Greyish, purplish red, RHS N77B.

*Venation pattern.*—Upper surface: Arcuate with a few pinnate. Lower surface: Reticulate.

*Color.*—Immature leaf: Upper surface: Red, RHS 183B. Lower surface: Purplish red, RHS N186D.

*Color.*—Mature leaf: Upper surface: Center=Greyish purple, RHS 187B; Flecking=Yellow green, RHS 144A. Lower surface: Greyish red, RHS N186C.

*Petiole length.*—4-5 cm.

*Petiole diameter.*—0.2-0.3 cm.

*Petiole color.*—Purplish red, RHS N79B.

*Petiole texture.*—Smooth, no pubescence.

Flowers and seeds: Not observed.

Fruit/Seed set: Not observed.

Disease and Insect Resistance: The disease and insect resistance of this cultivar is typical of its species. The most common insect pests observed on this plant in Gainesville, Fla. have been long-tailed or citrus mealybugs (*Pseudococcus* sp.), which occurred on older stock plant material that had been held in the greenhouse for over 3-4 months. Impatiens Necrotic Spot Virus (*Bunyaviridae*) has also been observed in plants that were confined in greenhouses with mixed crops (peppers) that were infected with Western flower thrips (*Frankliniella occidentalis*). The most common pathogen of this species in the U.S. is downy mildew (*Peronospora lamii*) and it has been observed in stock materials grown closely together during the cooler growing seasons.

What is claimed is:

1. A new and distinct *Plectranthus scutellarioides* plant called 'UF15-97-9' as shown and described herein.

* * * * *